United States Patent [19]

Furlan

[11] Patent Number: 4,897,408

[45] Date of Patent: Jan. 30, 1990

[54] WATER-SOLUBLE LYSINE SALTS OF (T)2-(4-FLUOROPHENYL)-ALPHA-METHYL-5-BENZOXAZOLE ACETIC ACID AND THEIR PREPARATION PROCESS

[75] Inventor: Diego Furlan, Milan, Italy

[73] Assignee: Euroresearch, s.r.l., Milan, Italy

[21] Appl. No.: 293,668

[22] Filed: Jan. 5, 1989

[30] Foreign Application Priority Data

Jul. 13, 1988 [IT] Italy ................... 19057A/88

[51] Int. Cl.$^4$ .................. C07D 263/56; A61K 31/42
[52] U.S. Cl. ..................... 514/375; 548/217
[58] Field of Search ............. 548/217; 514/375

[56] References Cited

U.S. PATENT DOCUMENTS

| | | | |
|---|---|---|---|
| 3,912,748 | 10/1975 | Evans | 548/217 |
| 3,988,466 | 10/1976 | Takagi et al. | 514/564 |
| 4,434,163 | 2/1984 | Lombardino | 514/226.5 |
| 4,652,654 | 3/1987 | Verga et al. | 548/217 |
| 4,749,694 | 7/1988 | Fix et al. | 514/203 |

OTHER PUBLICATIONS

Chem. Abstr., vol. 82, Entry 118774 b, 1975.

*Primary Examiner*—Donald D. Daus
*Attorney, Agent, or Firm*—Arnold, White & Durkee

[57] ABSTRACT

Water-soluble salts of (+)2-(4-fluorophenyl)-alpha-methyl-5-benzoxazole acetic acid with DL-lysine, D-lysine or L-lysine, suitable for the preparation of medicinal specialities such as syrups, creams, suppositories, aqueous solutions for personal hygiene etc, and their preparation process.

Said salts are obtained by suspending said acid in an organic solvent soluble or partly soluble in water, adding an equivalent quantity of said lysine and crystallizing the salt obtained.

2 Claims, No Drawings

WATER-SOLUBLE LYSINE SALTS OF (T)2-(4-FLUOROPHENYL)-ALPHA-METHYL-5-BENZOXAZOLE ACETIC ACID AND THEIR PREPARATION PROCESS

FIELD OF THE INVENTION

This invention relates to water-soluble salts of (+)2-(4-fluorophenyl)-alpha-methyl-5-benzoxazole acetic acid, hereinafter also called flunoxaprofen, which are suitable for the preparation of medicinal specialities such as syrups, creams, suppositories, aqueous solutions for personal hygiene etc, possessing anti-inflammatory, analgesic and antipyretic activity, and to their preparation process.

PRIOR ART (+)2-(4-fluorophenyl)-alpha-methyl-5-benzoxazole acetic acid is known both in its raceme form and in its dextrorotatory and levorotatory forms. It is also known to possess considerable anti-inflammatory, analgesic and antipyretic activity (J. Medic. Chem. 1975, vol 81, No. 1, pp 53–58). The dextrorotatory form is particularly active, demonstrating a much higher therapeutic index than known very active anti-inflammatories such as indomethacin and diclofenac (Italian patent No. 1,080,779).

However, because of its very limited water-solubility, flunoxaprofen encounters extremely serious limitations in the preparation of certain medicinal specialities such as syrups, creams, suppositories, aqueous solutions for personal hygiene, etc.

There is therefore a much-felt need for flunoxaprofen in water-soluble form.

SUMMARY OF THE INVENTION

We have now found that water-soluble salts of flunoxaprofen are obtained by salifying it with lysine, which can be used in raceme, dextrorotatory or levorotatory form.

The object of the present invention is therefore to provide flunoxaprofen salts with lysine in raceme, dextrorotatory or levorotatory form.

A further object of the present invention is to provide a process for preparing said salts, consisting of suspending the flunoxaprofen in an organic solvent soluble or partly soluble in water, quickly adding an equivalent quantity of lysine and crystallizing the salt obtained by cooling.

DETAILED DESCRIPTION OF THE INVENTION

To prepare the salts of the present invention, the flunoxaprofen is suspended in an organic solvent soluble or partly soluble in water, in a quantity of 200–350 g per 1000 ml of solvent.

The solvent is preferably chosen from the group consisting of $C_1$–$C_4$ alcohols, ketones such as acetone and methylethylketone, ethyl acetate and acetonitrile.

The flunoxaprofen suspension is heated to a temperature of between 20° and 80° C. and an equivalent quantity of lysine in raceme, dextrorotatory or levorotatory form in aqueous solution at a concentration of up to 60% by weight or in solid form with an $H_2O$ content of up to 10% by weight. A clear solution immediately forms. The salt of flunoxaprofen with lysine then precipitates at a temperature of between −5° and +30° C.

The salt is recovered by filtration, washed with the solvent and dried under vacuum at a temperature of between 50° and 70° C.

The salt obtained has a water-solubility at 20° C. of 100 g per 100 ml.

When subjected to pharmacological tests, the obtained salt demonstrates anti-inflammatory properties equal to flunoxaprofen itself, for an equivalent flunoxaprofen concentration.

The $LD_{50}$, $ED_{50}$ and TI (therapeutic index) values are given hereinafter for the salt of flunoxaprofen with DL-lysine compared with flunoxaprofen and diclofenac, which is a well-known very active anti-inflammatory.

The $LD_{50}$ was determined by the Litchfield-Wilcoxon method on mause using progressive oral doses. The $ED_{50}$ was determined by the test involving experimental edema induced by carrageen in a rat's paw (Sprague Dawley—Charles River): in this test the medicament is administered in 3 or 4 different progressive doses 60 minutes before inoculating 0.05 ml of a 1% carrageen solution under the plantar aponeurosis. The paw volume is checked 2, 4 and 6 hours after inoculating the carrageen.

The results obtained were as follows:

|  | $LD_{50}$ mg/kg | $ED_{50}$ mg/kg | TI $LD_{50}/ED_{50}$ |
|---|---|---|---|
| Salt of flunoxaprofen with DL-lysine | 720.0 (*) | 5.54 (*) | 129.96 |
| Flunoxaprofen | 723.5 | 5.97 | 121.18 |
| Diclofenac | 235.0 | 10.0 | 23.5 |

(*) expressed as flunoxaprofen

The salts according to the invention may be used for the preparation of pharmaceutical compounds added with common ingredients known in the pharmaceutical technique for obtaining syrups, creams, suppositories, aqueous solutions for person hygiene etc.

The following examples of the preparation of salts according to the invention are given for the purposes of non-limiting illustration.

EXAMPLE 1

285 g of (+)2-(4-fluorophenyl)-alpha-methyl-5-benzoxazole acetic acid are suspended in 1000 ml of isopropyl alcohol. The suspension obtained is heated to 60° C. under stirring and 292 g of a 50 weight% aqueous solution of DL-lysine are then quickly added. A clear solution is immediately obtained, and precipitation of the salt of (+)2-(4-fluorophenyl)-alpha-methyl-5-benzoxazole acetic acid with DL-lysine commences after a few minutes. The mixture is cooled to 0° C., filtered and the salt washed with isopropyl alcohol. The salt is then dried at 60° C. under vacuum.

428 g of the desired product are obtained with a melting point of 194°–196° C. and a water-solubility at 20° C. of 100 g per 100 ml.

The DL-lysine titre in the obtained salt is 33.8% and the (+)2-(4-fluorophenyl)-alpha-methyl-5-benzoxazole acetic acid titre is 66.1%.

EXAMPLE 2

Example 1 is repeated using 1200 ml of ethyl acetate as solvent, and L-lysine instead of DL-lysine.

425 g of salt are obtained having an L-lysine titre of 33.6% and a (+)2-(4-fluorophenyl)-alpha-methyl-5-benzoxazole acetic acid titre of 66.0%.

The water-solubility is as in Example 1.

EXAMPLE 3

Example 1 is repeated using 1200 ml of acetone as solvent and 146 g of D-lysine as reagent.

426 g of salt are obtained having a D-lysine titre of 33.8% and a (+)2-(4-fluorophenyl)-alpha-methyl-5-benzoxazole acetic acid titre of 66.0%.

The water-solubility is as in Example 1.

I claim:

1. Water-soluble salts of (+)2-(4-fluorophenyl)-alpha-methyl-5-benzoxazole acetic acid with DL-lysine, D-lysine or L-lysine.

2. Pharmaceutical compositions containing a salt of (+)2-(4-fluorophenyl)-alpha-methyl-5-benzoxazole acetic acid with DL-lysine, D-lysine or L-lysine as active principle.

* * * * *